United States Patent [19]
Scarberry et al.

[11] Patent Number: 5,222,478
[45] Date of Patent: Jun. 29, 1993

[54] APPARATUS FOR APPLICATION OF PRESSURE TO A HUMAN BODY

[76] Inventors: Eugene N. Scarberry, 208 Terrace Ct. Rd., Trafford, Pa. 15085; Patrick M. Handke, 416 Brunner Dr., Monroeville, Pa. 15146

[21] Appl. No.: 895,225

[22] Filed: Jun. 8, 1992

Related U.S. Application Data

[63] Continuation of Ser. No. 412,627, Sep. 27, 1989, abandoned, which is a continuation-in-part of Ser. No. 273,587, Nov. 21, 1988, abandoned.

[51] Int. Cl.⁵ ............................................. A61H 31/02
[52] U.S. Cl. .................................... 128/30.2; 128/28; 128/30
[58] Field of Search ............... 128/28, 30, 30.2, 24 R, 128/DIG. 20, 206.21, 206.24, 206.25, 206.26; 602/13

[56] References Cited

U.S. PATENT DOCUMENTS

| | | |
|---|---|---|
| 2,241,444 | 5/1941 | Bower . |
| 2,309,361 | 1/1943 | Terhaar .................. 128/30.2 |
| 2,480,980 | 9/1949 | Terhaar . |
| 2,899,955 | 8/1959 | Huxley, III et al. . |
| 3,043,292 | 7/1962 | Mendelson ............. 128/30.2 |
| 3,078,842 | 2/1963 | Gray . |
| 3,212,497 | 10/1965 | Dickinson ............. 128/DIG. 20 X |
| 3,577,977 | 5/1971 | Ritzinger, Jr. et al. . |
| 3,745,998 | 7/1973 | Rose . |
| 4,257,407 | 3/1981 | Macchi . |
| 4,366,815 | 1/1983 | Broomes . |
| 4,508,112 | 4/1985 | Seeler . |
| 4,523,579 | 6/1985 | Barry . |
| 4,617,921 | 10/1986 | Seeler . |
| 4,621,621 | 11/1986 | Marsalis . |
| 4,657,003 | 4/1987 | Wirtz ..................... 128/869 |
| 4,664,098 | 5/1987 | Woudenberg et al. . |
| 4,739,755 | 4/1988 | White ...................... 128/206.12 |

FOREIGN PATENT DOCUMENTS 2635454  2/1990  France ..................... 606/53

Primary Examiner—Richard J. Apley
Assistant Examiner—Linda C. M. Dvorak
Attorney, Agent, or Firm—J. Stewart Brams

[57] ABSTRACT

A respirator, resuscitator, wrap or sheath, breathing mask or the like which provides a closely form-fitting shell adapted to be disposed adjacent a portion of a human body to form intermediate the shell and the human body portion a thin section, minimal volume pressure containment chamber which receives pressures varying from ambient pressure for therapeutic purposes, and a corresponding method.

30 Claims, 2 Drawing Sheets

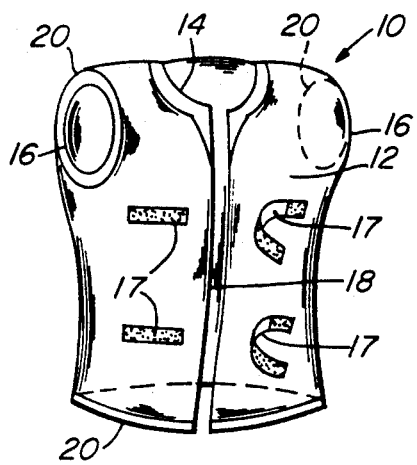
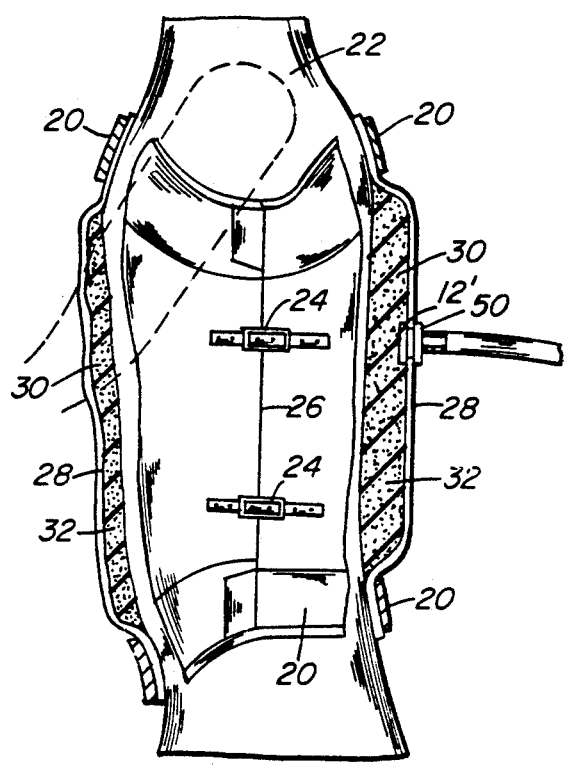
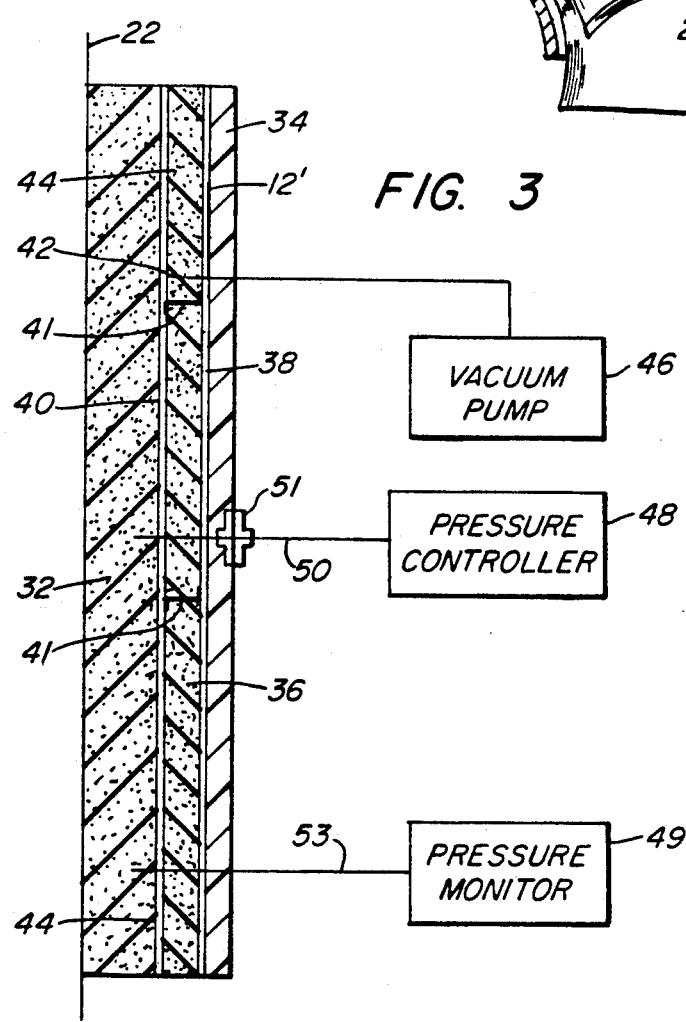

5,222,478

APPARATUS FOR APPLICATION OF PRESSURE TO A HUMAN BODY

This application is a continuation of co-pending application Ser. No. 07/412,627 filed on Sep. 27, 1989, now abandoned which is a continuation-in-part of application Ser. No. 07/273,587 filed Nov. 21, 1988, now abandoned.

BACKGROUND OF THE INVENTION

In the art of respirators, resuscitators, and the like it is well known to provide apparatus in the form of an enclosure which encompasses a portion of the human body such as the upper torso or thoratic region thereof to provide within the confines of the enclosure a pressure containment chamber wherein pressure variations may be applied to the body to stimulate respiration. A wide variety of such devices are known, the following prior art being representative.

U.S. Pat. No. 3,078,842 discloses a resuscitation apparatus which employs a rigid shell to enclose the torso of a human body. U.S. Pat. No. 4,523,579 discloses another rigid shell type body respirator having flexible side walls. U.S. Pat. No. 2,241,444 discloses a respirator jacket comprised of a rigid shell made by laying up reinforced plaster of parts material on a plaster cast which has been molded to the body contours of the individual user, and which includes an enlarged cavity confronting the chest and adjacent abdominal region of the user. Other rigid shell type resuscitators are disclosed by U.S. Pat. No. 4,257,407 and 2,309,361. The latter of these discloses a padded liner in a rigid generally form-fitting respirator.

U.S. Pat. No. 2,899,955 discloses a respirator belt which encircles the waist of a user and includes an inflatable bladder to which air pressure is directed for assisted breathing. U.S. Pat. No. 4,621,621 discloses a respirator including a rigid wire cage that encompasses a portion of a user's body and is in turn encompassed by an air tight cover to provide a vacuum chamber surrounding the user's body. U.S. Pat. No. 3,577,977 discloses a flexible, inflatable bladder-type jacket and U.S. Pat. 2,480,980 discloses a rigid, generally form-fitting respirator jacket. Finally, U.S. Pat. No. 4,664,098 discloses a cardio-pulmonary resuscitator which is worn by a patient in the manner of a belt encompassing the abdominal region.

Notwithstanding such known devices, practitioners in the art have continued to seek improved body respirators. For example, improvements have been continually sought in body respirator compactness, portability, user comfort, reduced power requirements, and of course improved therapeutic efficacy.

Also known in the prior art are a variety of vacuum devices for immobilizing a part of a body. The Rapid Form ™ brand vacuum splint is one example. Such devices utilize a structure known as vacuum beads to provide a selectively rigid or flexible member that is used, for example as in the case of the above specified vacuum splint, to immobilize selected body parts that have sustained bone fractures or the like. Such known devices generally comprise a thin section airtight envelope filled with material such as styrofoam beads which interengage and deform upon application of a vacuum within the envelope to thereby render the vacuum bead material relatively rigid. The rigid vacuum bead material thus is utilized to immobilize a selected body part.

BRIEF SUMMARY OF THE INVENTION

The present invention contemplates a novel and improved body respirator, resuscitator, pressure or pulse monitoring apparatus or similar apparatus such as a wrap or sheath, or a breathing mask which is universal in its application by virtue of its being very closely form-fitting for any selected user irrespective of variations in body size or contours from one user to another. The invention also is light in weight and compact, imposes minimal power requirements for its use, and provides greatly enhanced user comfort and therefore enhanced user tolerance. The invention thus provides greatly enhanced convenience for the user as well as for emergency rescue teams and others who may encounter the need for regular access to emergency equipment of this sort, among other advantages. The invention also contemplates a novel and improved method for the use of varying pressures in a variety of medical applications.

The apparatus of this invention contemplates, in one of several presently preferred embodiments, a body enclosure comprised of a sheath or wrap of selectively flexible or rigid material, such as the above characterized vacuum bead structure or the like, formed to encompass a selected body portion and including seals to seal perimeteral portions or other portions of the body sheath, for example to seal about the openings through which adjacent body portions project such as at the waist, neck, or arms.

The sheath is adapted to be placed in closely spaced form-fitting relation encompassing a portion of the user's body to define, in a zone between the sheath and the user's body, a very thin-section chamber or space. The sheath is then selectively rigidified, as by application of a vacuum if comprised of conventional vacuum bead material, to form a rigid, form-fitting enclosure about the encompassed portion of the patient's body whereby the chamber or space between the sheath and the user's body is provided with a rigid outer wall which closely conforms to the adjacent body contours of the user. Pressure or vacuum generating equipment may be utilized to apply pressure variations within this space to act on the flexible inner wall (i.e. the user's body) to assist user ventilation or for other purposes. Alternatively, the pressure within the space may be observed to monitor user pulse, breathing, or the like.

Because the sheath is selectively rendered rigid or flexible, it is quite compact and easily stored when not in use. Because it is placed about the user's body in a flexible state, it is universal in application and extremely closely form fitting with the attendant benefit that the containment space defined between the sheath and the user's body is of minimal volume. Effective operation thus is achieved with minimal power requirements and minimal required compressor or vacuum pump delivery rates.

The invention additionally contemplates spacer means disposed within the pressure containment space between the sheath and the user's body so as to define a predetermined minimal spacing therebetween so that the form and volume of the pressure containment space may be readily controlled. The spacer means is of a structure (e.g. open cell foam) to permit pressure variations introduced at one point within the containment space to be transmitted throughout the space even if the spacer means is substantially co-extensive with the pressure containment space.

The invention additionally contemplates a novel and improved method of fluid pressure utilization in conjunction with the body of a user with advantages corresponding to the above noted and other advantages of the novel apparatus.

It is accordingly one object of our invention to provide a novel and improved body respirator, resuscitator, or the like.

It is a further object of our invention to provide an improved apparatus and method for the utilization of external pressure in the medical treatment of a patient.

A more specific object of the invention is to provide a selectively rigid or flexible body wrap sheath, mask, vest, or similar apparatus which is adapted to encompass a portion of a body to thereby define in conjunction therewith a sealed space adjacent the body such that pressure controlling or monitoring means cooperable with the sheath is operable to selectively vary or monitor the pressure within the sealed space.

BRIEF DESCRIPTION OF THE DRAWINGS

These and other objects and further advantages of my invention will be more readily understood upon consideration of the following detailed description and the accompanying drawings, in which:

FIG. 1 is a frontal elevation of one presently preferred embodiment of our invention;

FIG. 2 is a side elevation, partially broken away to show details of an alternative embodiment of our invention shown encompassing the body of a user;

FIG. 3 is an enlarged detailed portion of FIG. 2 including schematic representation of a vacuum pump and pressure controller according to one presently preferred embodiment of the invention;

Figure 4:
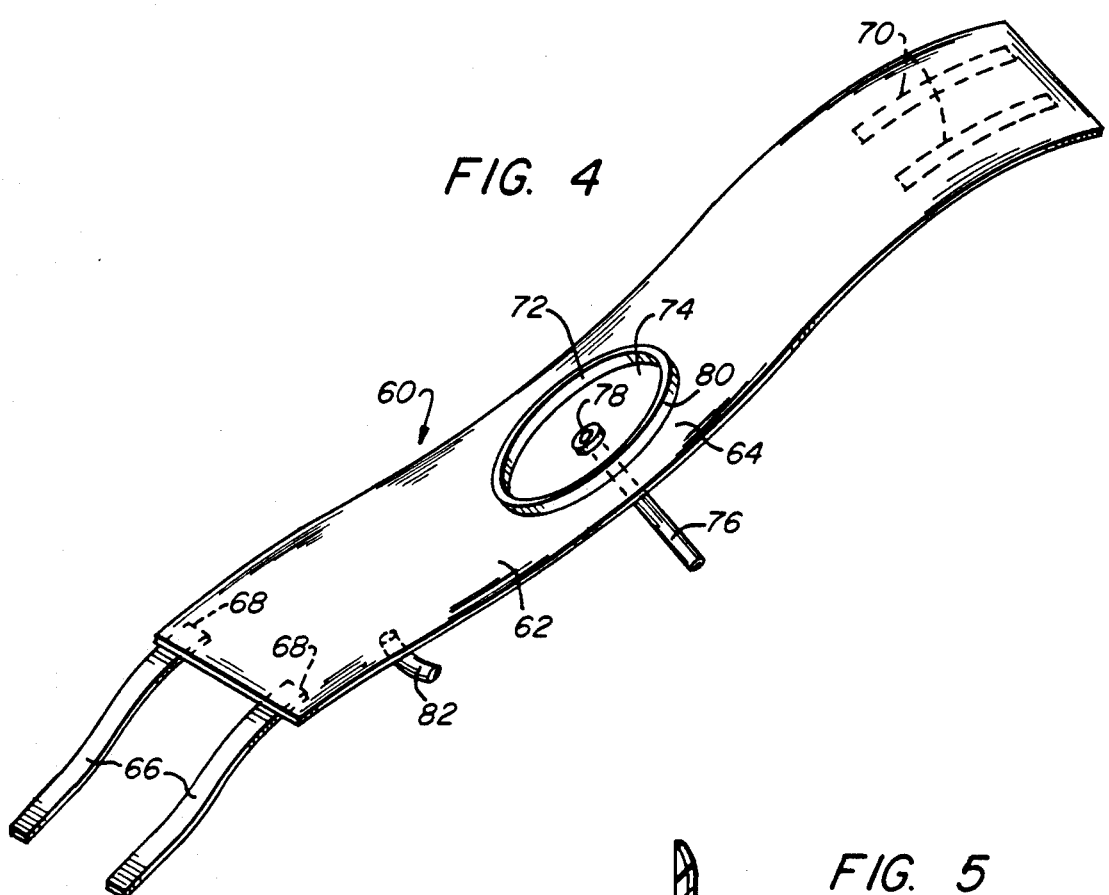
FIG. 4 is a perspective view of a wrap or sheath apparatus according to an alternative embodiment of the invention.

There is generally indicated at 10 in FIG. 1 a body respirator or the like constructed according to one presently preferred embodiment of our invention and including a body sheath 12 formed for purposes of this embodiment as a vest or jacket and including, when enclosed about the user's body, a neck opening 14 as well as arm holes or apertures 16.

Suitable fasteners are provided, for example Velcro TM or similar interengaging tapes, to maintain a front opening 18 tightly closed and sealed when the vest is donned and in use, and to thus maintain the sheath 12 in closely form-fitting relation about the upper torso or thoratic region of the user's body.

An alternative form of the sheath or vest as identified at 12' in FIG. 2 passes beneath the arms of the user so no arm holes are required. The sheath 12' encompasses the user's waist and upper chest. For the embodiments shown in FIGS. 1 and 2, all openings from which parts of the user's body project are sealed by suitable seal means such as encompassing band means 20 to form intermediate the sheath and the body 22 (FIG. 2) of the user a sealed space or chamber 32.

Other differences of the FIG. 2 embodiments from that of FIG. 1 include buckle and strap fasteners 24 in lieu of fasteners 17 and the location of closure 26 adjacent one side of the user's body rather than extending vertically along user's front as does opening 18 of the FIG. 1 embodiment. Of course, a wide variety of alternative configurations may be utilized in accordance with the specific purposes and desired features of the sheath 12. Specifically, an apparatus according to this invention but adapted to encompass a body part other than the chest or abdominal region will of course be configured accordingly.

Regarding further aspects of the invention, as exemplified by FIG. 2, sheath 12' comprises a selectively rigid or flexible wall system 28 which is maintained in closely spaced relationship with respect to the user's body 22 as by means of spacers 30, which may be of such suitable structure as open cell foam to permit the transmission of pressure variations imposed at one location within the confines of the sheath 12' to all locations therein.

The spacers 30 may occupy only a small portion or alternatively substantially all of the volume of the space 32 defined intermediate sheath 12' and the user's body 22, within the confines of perimeteral seals 20. It will be noted, however, that space 32 need not be coextensive with the mutually contiguous zones of sheath 12' and the user's body 22, that spacers 30 may be of other suitable structure or may be eliminated entirely, and that seals 20 need not be disposed about perimeteral portions of the sheath 12' where portions of the user's body extend therefrom.

The invention thus contemplates an apparatus which is utilized to form a sealed space between a body sheath and a user's body with the sealed space being defined generally by an inner wall system comprised of a portion of the user's body, an outer wall system comprised of a corresponding adjacent portion of a sheath wall disposed in closely spaced form-fitting relation with respect to the user's body. A seal system seals all interfaces between the sheath and the user's body that are exposed to pressure variations introduced within the sealed space.

It is noted that seals are to be provided to seal any opening which is provided to facilitate installation or removal of the sheath, for example opening 18 of FIG. 1 or 26 of FIG. 2. These and any other such openings would require seals to preclude leakage due to a pressure differential between ambient and the pressure condition within space 32.

There is shown in FIG. 3 a portion of my novel body respirator. In FIG. 3, sheath 12' is comprised of an outer flexible shell 34 of sheet polyethylene for example, which is coextensive with the selectively rigidified structure 36. Structure 36 comprises a pair of flexible, closely spaced, air impermeable inner and outer walls 38 and 40 of such suitable material as vinyl or polyeurethane impregnated nylon. The inner and outer walls 38 and 40 are sealed together along a continuous line encompassing a space 42 therebetween, which space 42 contains a mass of interengageable elements 44 such as beads of styrofoam plastic. Air permeable partition elements 41 joined to and extending between walls 40 and 38 may be provided at intervals in space 42 as barriers to prevent undesirable migration of beads 44 within the space 42.

As is known, the above described structure is typical of vacuum bead type systems wherein the application of a vacuum within space 42, as by means of a vacuum pump 46, causes walls 40 and 38 to collapse inwardly under the impetus of external ambient air pressure against the beads 44. Thus, upon imposition of such a vacuum in space 42, the styrofoam beads 44 deform in interengagement and lock up in an immobilized state to form a rigid shell from the previously flexible shell. Upon release of the vacuum drawn within space 42, the styrofoam beads 44 are released from their mutual interengagement and the vacuum bead structure 36 becomes once again flexible.

Carried adjacent the inner wall 40, and preferably affixed thereto in a suitable manner is the spacing material 32 as above characterized. In use, the innermost extent of the spacing material 32 engages the body of the user 22 to thereby establish and maintain a generally uniform spacing or separation between the sheath 12' and the user's body 22.

Of course, the spacing therebetween is uniform only if the spacer element 32 is of uniform thickness. More generally, the spacing between sheath 12' and user's body 22 may vary according to variation in the thickness of the spacing elements 32. Also, and as noted hereinabove, the spacing element 32 may be omitted entirely as it is contemplated that only a very thin section space generally is necessary between the user's body and the sheath 12' for effective operation of the invention.

As further shown in FIG. 3, the invention additionally comprises a pressure controller 48 which is powered by any suitable and conventional power means to deliver air flow under pressure to space 32 in order to impose within space 32 controlled pressure at variance with ambient atmospheric pressure. For example, pressure controller 48 may be utilized to impose alternating or cyclic elevated pressure within space 32, or a partial vacuum.

In order to accommodate the pressure controller 48, a suitable air flow delivery conduit 50 provides an air flow path between pressure controller 48 and space 32, and of course therefore traverses the sheath 12'. In a preferred embodiment the sheath 12' will include a port means having any suitable, known coupling 51 or air conduit connection on the outer side thereof for connection to a delivery conduit from pressure controller 48.

For emphasis it is reiterated here that the apparatus of this invention may take any of a variety of forms to encompass any portion of a user's body other than the chest or thoracic region and for a variety of purposes other than respiratory assistance. For example, an apparatus similar in many salient respects to that above described and encompassing the thoratic region may be utilized with alternating pressure, and in conjunction with alternating pressure delivered in a specified phased relationship to the airway of a patient to function as a heart pump for cardio-vascular resuscitation. In another alternative mode of use, the apparatus of this invention may be utilizied with pressure monitoring equipment 49 (FIG. 3) which is connected via a conduit 53 to space 32 for the purpose of monitoring pressure therein. Thus any physical response of a user which causes variation of the pressure within space 32, pulse or spontaneous breathing for example, may be observed by use of pressure monitor 49. The invention may also be embodied as a wrap or sheath as above mentioned, for example a wrap or sheath for a limb or other extremity. In FIG. 4 I have shown such a wrap or sheath 60 which is adapted to encompass a human limb or any similarly configured body part, for example, the neck. The sheath 60 is comprised of an elongated flexible band 62 which forms an elongated, thin section envelope 64 that contains therein material such as styrofoam beads similar in all salient respects to the above described vacuum bead structures.

Fastener bands 66 are affixed adjacent one longitudinal end of band 64 as by stitching 68 and cooperating fastener strips 70 are similarly affixed adjacent the opposed end of band 62. Fastener strip 66 and 70 may be cooperating hook and loop type fastener strips such as Velcro TM brand fastener material.

Sheath 60 may also include seal means such as a patch seal 72 in the form of a foam rubber or similar sealing strip affixed to one side of band 62 intermediate its longitudinal ends and forming thereon a closed perimeter which defines within its confines a space 74. A suitable vacuum connection 76 communicates with space 74, for example by penetrating the band 62 via a fitting 78 within the confines of seal 72. The sheath 60 thus may be applied to a human limb or similarly configured body part as a wrap with the fastener strips 66 and 70 overlapping to maintain the band 62 in encompassing relationship on such a body part and with an outer seal surface 80 of seal member 72 engaging a corresponding surface portion of such body part continuously along the extent of seal 72. By application of vacuum as via a vacuum connection 82, the band 62 may be selectively rigidified in encompassing relationship about a human limb as described. In an alternative embodiment, the selectively rigidified part of band 62 may be limited to that part encompassed by seal 72.

For either embodiment, the application of vacuum to the band 62 as described forms a relatively rigid outer wall for space 74 with the inner wall thereof being that portion of the patient's body encompassed by seal 72. Accordingly, pressures varying from ambient atmospheric pressure may be applied for therapeutic effect to that portion of the patient's body exposed to such pressure variation within the confines of seal 72 in much the same manner as pressure variations are applied to the upper thoracic region as above described with reference to FIGS. 1 through 3.

Specifically, since the outer wall of space 74 is rigid, the application of elevated pressure above ambient pressure via connection 76 in space 74 will tend to compress the corresponding adjacent portion of the patient's body which forms the inner wall of space 74 whereas a partial vacuum within space 74 will tend to distend the adjacent body portion by drawing it into the space 74.

Figure 5:
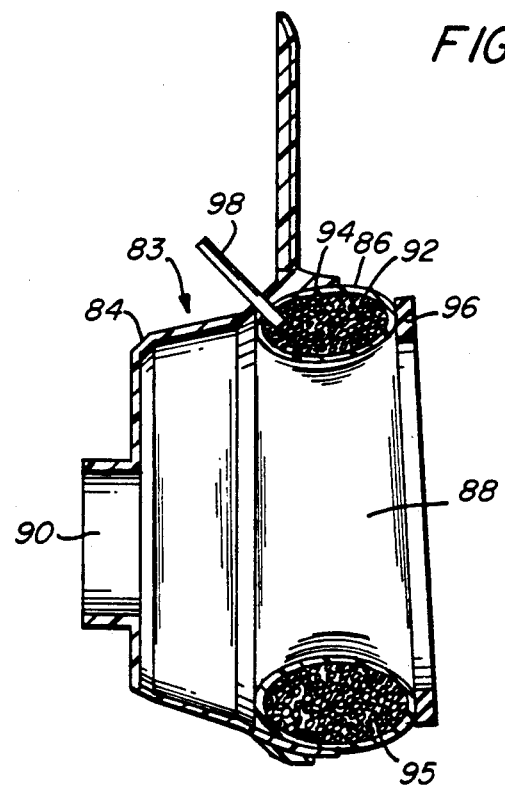
FIG. 5 is a sectioned side elevation of a breathing mask or similar apparatus according to another alternative embodiment of the invention.

Another alternative embodiment of the invention is shown in FIG. 5 as a breathing mask 83 having a generally rigid body 84 which carries a seal assembly 86 that encompasses an open space 88 which communicates through body 84 with a gas supply connection portion 90 of mask body 84. Accordingly, mask 83 may be placed with seal assembly 86 in confronting engagement with a user's face so that seal assembly 86 encompasses the nose or the nose and mouth of a user. Breathing gas for the user is then supplied exclusively through connection 90.

Since the function of a breathing mask such as shown in FIG. 5 differs from the function of a body type respirator such as shown in FIGS. 1 through 3, the expanse of space within the confines of seal 86 need not be enclosed by the vacuum bead material to provide a rigid outer wall such as is required for the respirator of FIGS. 1 through 3. Rather, for the FIG. 5 embodiment of the invention, the function of vacuum bead structure as described hereinbelow is to provide an effective and and closely conforming surface seal to fit a wide variety of user facial contours in more or less universal fashion whereby a single mask may be readily adapted for use by virtually any patient.

Accordingly, it will be seen that seal assembly 86 comprises a flexible perimeteral wall system 92 comprised of rubber for example, and formed in a closed ring with a generally tubular cross section. The space 94 closed within the wall system 92 is filled preferably with vacuum bead material such as above described with reference to FIGS. 1 through 3, for example styrofoam plastic beads.

The resilient wall element 92 is mounted upon mask body member 84 and extends outwardly therefrom, and a seal member 96 may be affixed to an outer extent of wall element 92 for confronting sealing engagement with a user's face. A vacuum connection 98 is provided to permit drawing a partial vacuum upon space 94 with seal 96 in engagement with that portion of a user's face encompassing the nose or the nose and mouth. The partial vacuum, acting on the mass of interengageable bends, causes them to become forcefully interengaged under the impetus of ambient atmospheric pressure compressing the flexible wall element 92 inwardly. The mass of beads thus becomes rigid and supports the wall 92 against inward collapse. The wall 92 thus holds whatever form it and the contained beads have assumed by virtue of sealing pressure against the face of a user. Accordingly, the mask 83 is effective universally for any user as the seal thereon readily conforms, and is maintained in conforming relationship to the user's face by virtue of operation of the vacuum bead apparatus as described.

For purposes of this invention, including all embodiments described hereinabove, the structure of the vacuum bead material may include a variety of alternatives including styrofoam beads as above described or alternatively a finely divided powder with similar mechanical properties. Additionally, the material within the vacuum envelope may be infused or coated with a bonding agent such as a heat curing adhesive to permit the set or shape of the vacuum bead structure, once established by the vacuum action, to be permanently maintained. This is done by subjecting the vacuum bead material to sufficient activating or curing energy such as heat for curing a heat cured adhesive. Other types of bonding systems may also be used, for example chemical curing systems pressure sensitive adhesives, photo sensitive or light curing systems, and so forth. Any adhesive will suffice which provides the function of maintaining the shape or form of the vacuum bead structure after release of the vacuum by bonding the individual vacuum beads or similar elements together. Some adhesive systems, such as heat curing or heat setting adhesives, would for all practical purposes be limited to use in a structure as described which is to be permanently maintained in the form suited to a particular user. That is, once the heat setting adhesive is cured, it would not be possible to re-use the same adhesive. By contrast, a hot melt adhesive or similar bonding system would permit re-use of a mask or respirator structure according to this invention for another user as the bonds between interengaged vacuum beads could be broken by mechanical force (i.e. massaging or kneading the vacuum bead envelope). The mask or respirator could then be fitted to a different user, the vacuum applied to maintain the resulting seal and/or space configuration, and the vacuum bead material then once again subjected to heat to melt the adhesive and bond the vacuum bead materials in the new configuration.

The seal 96 of FIG. 5 or corresponding seal elements from other disclosed embodiments similarly may take a variety of forms including a rubber surface seal as shown, or alternatively an inflated bladder seal filled with air, foam or gel, a flap seal, or the like. Any of these may include a tacky outer surface for engagement with the respective body part of a user to provide sealing with a user's body in part by temporary, releasable adhesion to the skin. Another seal structure contemplated includes a closed envelope containing a hydroscopic gel material which has cushioning properties and a tacky character such that the seal is resilient at low mechanical loads but is permanently deformed by larger loads. The air filled bladder seal generally may be a tubular bladder with air space encircling a space similar to 94 that contains therein vacuum beam material or any alternative as above discussed. In addition, it is contemplated that the outer surface of wall 92 may function itself as a seal for confronting engagement with a body portion of a user such that a separate seal member such as at 96 in FIG. 5 may be entirely eliminated.

In an additional alternative embodiment applicable to any of the above described structures, the invention may be comprised of a body member which carries a separate, replaceable vacuum bead liner structure as opposed to having the vacuum bead structure permanently installed with other elements of the invention.

One advantage of the mask structure of FIG. 5 is that when vacuum is applied via connection 98, the vacuum bead material 95 will be maintained in a rigid form defining an outer profile for sealing in close conformity to the face of a user; however, if leaks should be present in such a seal, the vacuum bead material 95, even when under vacuum, can be formed or molded by the application of mechanical pressure (i.e. finger pressure) to change the seal profile or configuration. Accordingly, if leaks are detected after application of vacuum, the medical practitioner can eliminate such leaks with mere finger pressure applied against wall element 92 adjacent the leak. Such mechanical pressure will displace the wall 92 inwardly thus moving or displacing the immediately adjacent vacuum beads. Since under such relatively small and non-uniform mechanical pressures the individual beads are not significantly compressed but merely redistributed, mechanical finger pressure as described will force some of the vacuum bead material outwardly in the direction of seal 96 to thereby close the leak. Thus, with the combination of direct fitting to the face of the user, application of vacuum to maintain resulting shape, application of mechanical pressure as needed to effect proper seal conformity with the user's face, and finally application of heat or other mechanism to set an adhesive supplied within space 94 to the vacuum bead material 95, the mask 83 provides for a custom fit to any user, which custom fit is then maintained indefinitely for as long as that user must use the mask. The same mask may then be reused to fit any other user with a similar custom fit to provide seal integrity of equal quality.

In still another alternative embodiment of the invention, the vacuum bead material 95 may be supplanted entirely by a heat cure or similar adhesive in powder, granular or bead-like form. Although such a structure is believed to be less useful for repeated universal applications, it would be the equal of other above described embodiments for providing a closely conforming seal in a single use for any user irrespective of differences in facial contours.

Entirely similar structural alternatives as above disclosed also are contemplated for the embodiments of FIGS. 1 through 4 inclusive, and for still further embodiments not heretofore discussed. For example, the disclosed mask structure also contemplates such alternatives as a mask effectively functioning as a perimeteral seal with nasal cannulae protruding within space 88 to be received into the nares of a user.

From the above description, our novel method will also be apparent as including, inter alia, the steps of encompassing or enclosing a patient's body portion with a flexible structure including a seal to provide sealing against selected body portions to form a chamber or enclosed space, and rigidifying at least a part of the structure to provide a rigid boundary for a corresponding part of the enclosed space then one may, selectively vary the pressure condition within the enclosed space from ambient either at will or in a predetermined program of pressure variation, or by voluntary or involuntary patient response, and as a further optional step, such pressure variation occurring within the enclosed space may be monitored.

According to another aspect of our novel method, the encompassing of a patient's body portion with a flexible sheath as hereinabove specified may be performed as a treatment for obstructive sleep apnea. Sleep apnea is a widespread sleep disorder estimated to affect up to 3% or more of the general population and commonly characterized by occlusion of the upper airway in sleep with resultant disruption of breathing and sleep patterns, and potential serious consequences including oxygen starvation.

The method of our invention accordingly contemplates the application of negative pressure (i.e. pressure below ambient atmospheric) at least to frontal areas of a patient's neck to thereby draw out or distend the adjacent tissue thus permitting the relatively elevated ambient pressure in the airway, or artificially elevated pressure therein such as CPAP (continuous positive airway pressure), to expand or distend the upper airway thereby relieving airway occlusion.

According to the description hereinabove there is provided by the instant invention a novel and improved method and apparatus for the external application of pressure variations to a portion of a user's body. The invention may be utilized to apply pressure at decreased or elevated magnitude with respect to ambient, or in a program of varying pressure magnitudes applied by automatic or manual control, or even pressure variations from ambient or from elevated or decreased pressure magnitudes resulting from voluntary or involuntary user response. The invention further contemplates the monitoring of any such pressure magnitude or variation thereof.

The invention also contemplates an apparatus comprised of separate inner garment, vacuum bead shell, and outer garment structures. The inner garment may be, for example, a foam rubber shell bonded to a fabric backing for the purpose of separating the vacuum bead structure from the user's body. The outer garment may be of the character above described with reference to flexible shell 34, and may include all of the requisite seals such as the described seals 20. Thus it will be clear that the above described components of the invention may be integrally formed together, formed separately and permanently or separably connected, or formed and used separately to make up a flexible body enclosing sheath apparatus as above described.

I have contemplated various other alternative and modified embodiments apart from those specified hereinabove, and certainly such would also occur to others versed in the art once apprised of my invention. Accordingly, the invention is to be construed broadly and limited only by the scope of the claims appended hereto.

I claim:

1. An apparatus for applying external pressure variation to a given body portion of a user's body comprising:
    a sheath means adapted to be retained with respect to the given body portion;
    said sheath means including a flexible portion which is adapted to be formed into a selected shape which closely conforms with the given body portion to provide a closely form-fitting enclosure which envelopes the given body portion at essentially a minimum spacing therefrom when said sheath means is retained with respect to the given body portion;
    said sheath means including seal means which is operable to engage the user's body to form within said form-fitting enclosure an enclosed space intermediate said sheath means and the given body portion;
    connection means communicating with said enclosed space and adapted to be connected to a pressure medium source for applying the pressure of a pressure medium at variance from ambient atmospheric pressure within said enclosed space; and
    means operable for selectively rigidifying said flexible portion when retained with respect to the given body portion in a manner that upon said selectively rigidifying, said flexible portion is maintained in said selected shape to provide said closely form fitting enclosure at said essentially minimum spacing throughout application of pressure within said enclosed space.

2. The apparatus as set forth in claim 1 additionally including pressure control means cooperable with said sheath means to selectively vary the magnitude of pressure within said enclosed space.

3. The apparatus as set forth in claim 1 additionally including pressure transmitting spacer means cooperable with said sheath means to limit the approach of said flexible portion toward the given body portion and to thereby define said minimum spacing.

4. The apparatus as set forth in claim 3 wherein said spacer means is substantially mutually coextensive with said enclosed space.

5. The apparatus as set forth in claim 4 wherein said spacer means includes porous means having sufficiently open porosity to permit the pressure medium to be distributed substantially throughout said enclosed space.

6. The apparatus as set forth in in claim 4 wherein said flexible portion is essentially coextensive with said sheath means.

7. The apparatus as set forth in claim 1 wherein said seal means includes means cooperable with said sheath means to maintain a selected portion of said sheath means in sealed engagement with the user's body to form said enclosed space.

8. The apparatus as set forth in claim 1 additionally including adjustable retention means which is cooperable with said sheath means to permit said sheath means to be retained with respect to the given body portion.

9. The apparatus as set forth in claim 1 wherein said means operable for selectively rigidifying said flexible portion includes a flexible, wall portion of said sheath means enclosing a sealed chamber and a plurality of interengageable elements confined within said sealed chamber, and means communicating with said sealed chamber and adapted to communicate with a vacuum pump means for drawing a partial vacuum within said sealed chamber to thereby engage said interengageable elements in essentially rigid mutual interengagement.

10. The apparatus as set forth in claim 9 additionally including an outer flexible wall portion which is coextensive with said flexible portion and said outer flexible wall portion carrying adjacent at least a portion of its perimeter a portion of said seal means.

11. The apparatus as set forth in claim 10 additionally including air flow conveying conduit means traversing said sheath means and cooperable with said pressure medium source to provide air flow to and from said enclosed space.

12. The apparatus as set forth in claim 1 additionally including pressure monitoring means cooperable with said sheath means to monitor the pressure within said enclosed space.

13. The apparatus as set forth in claim 1 wherein said sheath means comprises a respiratory assistance apparatus adapted to encompass the upper torso of a human body for application thereto of such pressure to effect respiratory assistance.

14. The apparatus as set forth in claim 1 wherein said sheath means comprises a resuscitation apparatus adapted to encompass the upper torso of a human body for application thereto of such pressure to effect cardiopulmonary resuscitation.

15. An apparatus for enclosing a selected body portion of a human body comprising:
an enclosing means which is adapted to confront the selected body portion;
seal means associated with said enclosing means and operable to encompass a peripheral extent of the selected body portion and to sealingly engage said peripheral extent in a manner to define an enclosed space which extends adjacent the selected body portion and is enveloped by said enclosing means;
said enclosing means including a flexible portion which is adapted to be formed into a selected shape which closely conforms with at least a corresponding adjacent part of the selected body portion to provide a closely form-fitting enclosure which envelopes said corresponding adjacent part of the body portion at essentially a minimum spacing therefrom;
means operable for selectively rigidifying said flexible portion in a manner that upon said selective rigidifying said flexible portion is maintained in said selected shape; and
pressure medium connection means communicating with said enclosed space and adapted to be connected to a pressure medium source to provide within said enclosed space pressure at variance from ambient atmospheric pressure for application to the selected body portion.

16. The apparatus as set forth in claim 15 wherein said flexible portion includes a flexible wall means defining a sealed containment and a plurality of interengageable means disposed within said containment.

17. The apparatus as set forth in claim 16 wherein said means in rigidifying said flexible portion includes means for drawing a partial vacuum within said containment to permit ambient air pressure acting on said flexible wall means to move said interengageable means into mutual interengagement.

18. The apparatus as set forth in claim 17 additionally including adhesive means which is effective to maintain said interengageable means in mutual interengagement upon release of said partial vacuum within said containment.

19. The apparatus as set forth in claim 18 wherein said adhesive is a heat curing adhesive co-mingled with said interengageable means within said containment.

20. The apparatus as set forth in claim 18 wherein said adhesive means is a hot melt adhesive co-mingled with said interengageable means within said containment.

21. The apparatus as set forth in claim 18 wherein said interengageable means and said adhesive means are common integral units comprised of a plurality of discreet particles of adhesive.

22. The apparatus as set forth in claim 17 wherein said interengageable means includes a plurality of solid particles.

23. The apparatus as set forth in claim 22 wherein said solid particles are of a size that they collectively exhibit the character of a volume of powder.

24. The apparatus as set forth in claim 22 wherein said solid particles are of a size that they collectively exhibit the character of a volume of granulated matter.

25. The apparatus as set forth in claim 22 wherein said solid particles are of a size that they collectively exhibit the character of a mass of discreet beads of matter.

26. The apparatus as set forth in claim 22 wherein said plurality of solid particles includes a plurality of discreet styrofoam particles or layers of material.

27. An apparatus for enclosing a selected body portion of a human body comprising:
an enclosing means which is adapted to confront the body portion;
said enclosing means including a flexible portion which is adapted to be formed into closely conforming relation with respect to at least a corresponding adjacent part of the body portion;
first rigidifying means selectively operable to temporarily rigidify said flexible portion to maintain said closely conforming relation of said flexible portions with said corresponding adjacent part of the body portion; and
second rigidifying means operable to maintain the rigidity of said flexible portion in said closely conforming relation with said corresponding adjacent part of the body portion after release of said first rigidifying means.

28. The apparatus as set forth in claim 27 wherein said flexible portion includes a flexible wall means defining a sealed containment and a plurality of interengageable means disposed within said containment.

29. The apparatus as set forth in claim 28 wherein said first rigidifying means includes means for drawing a partial vacuum within said containment to permit ambient air pressure acting on said flexible wall means to move said interengageable means into mutual interengagement.

30. The apparatus as set forth in claim 29 wherein said second rigidifying means includes adhesive means which is effective to maintain said interengageable means in said mutual interengagement upon release of said partial vacuum within said containment.

* * * * *

UNITED STATES PATENT AND TRADEMARK OFFICE
CERTIFICATE OF CORRECTION

PATENT NO.   :   5,222,478
DATED        :   June 29, 1993
INVENTOR(S)  :   Eugene N. Scarberry, Patrick M. Handke It is certified that error appears in the above—identified patent and that said Letters Patent is hereby corrected as shown below:

In claim 5 (column 10, line 50) delete "the."

In claim 17 (column 11, line 64) delete "in" and substitute -- for --.

Signed and Sealed this

Nineteenth Day of March, 1996

Attest:

BRUCE LEHMAN

*Attesting Officer*           *Commissioner of Patents and Trademarks*